(12) United States Patent
Naeff et al.

(10) Patent No.: US 6,645,522 B2
(45) Date of Patent: *Nov. 11, 2003

(54) ERYTHROPOIETIN LIPOSOMAL DISPERSION

(75) Inventors: Rainer Naeff, Langwiesen (CH); Sandro Delmenico, Schaffhausen (CH); André Wetter, Schaffhausen (CH); Frank-Ulrich Floether, Schaffhausen (CH)

(73) Assignee: Cilag AG (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 2 days.

(21) Appl. No.: 09/252,563

(22) Filed: Feb. 18, 1999

(65) Prior Publication Data

US 2002/0028236 A1 Mar. 7, 2002

(30) Foreign Application Priority Data

Feb. 23, 1998 (EP) .............................................. 98103111

(51) Int. Cl.⁷ .............................................. A61K 9/127
(52) U.S. Cl. ......................................... 424/450; 514/21
(58) Field of Search ............................. 424/450; 514/21

(56) References Cited

U.S. PATENT DOCUMENTS

| | | | |
|---|---|---|---|
| 5,569,464 A | 10/1996 | Endo et al. | |
| 5,618,698 A | 4/1997 | Lin | |
| 5,858,397 A | * 1/1999 | Lim .......................... | 424/450 |

FOREIGN PATENT DOCUMENTS

| | | | |
|---|---|---|---|
| EP | 253619 | | 7/1987 |
| EP | 0253619 A | | 1/1988 |
| JP | 61097229 | * | 5/1986 |
| JP | 5302925 | | 4/1992 |
| JP | 6228012 | | 1/1993 |
| JP | 08231417 | * | 9/1996 |

OTHER PUBLICATIONS

Maitani in J. of Pharm. Sciences. 85 # 4, Apr. 1996.*
Journal of Pharmaceutical Sciences, vol. 85, No. 4, Apr. 1996, pp. 440–445.
Oral Administration of Recombinant Human Erythropoietin in Liposomes in Rats: Influence of Lipid Composition and Size of Liposomes on Bioavailability.
Copy of European Search Report for Application No. 98 10 3111.
Database WPI, Section Ch. Week 9646, Derwent Pubs. Ltd., Class B04, AN96–461276. XP002073043 and JP Abstract JP08231417 (Chugai Pharm. Co. Ltd.) Sep. 1996.
Xian–Rong Qi et al.: "Evaluation of Liposomal Erythropoietin Prepared with Reverse–Phase Evaporation Vesicle Method by Subcutaneous Administration in Rats", Chemical and Pharmaceutical Bulletin, vol. 43, No. 2, Feb. 1, 1995, XP000494628.

* cited by examiner

Primary Examiner—Gollamudi S. Kishore
(74) Attorney, Agent, or Firm—Joseph S. Kentoffio

(57) ABSTRACT

The present invention relates to a liposome based formulation of erythropoietin comprising:
 (a) an effective amount of an erythropoietin;
 (b) a lipidic phase comprising:
  (i) lecithin or hydrogenated lecithin;
  (ii) optionally, a charged electropositive or electronegative lipid compound; and
  (iii) cholesterol or a derivative thereof selected from cholesterol esters, polyethylene glycol derivatives of cholesterol (PEG-cholesterols), and organic acid derivatives of cholesterols; and
 (c) a phosphate buffer.

The liposome based parenteral dosage form of the invention is prepared by means of an ethanol injection technique. The composition avoids the need for use of human serum albumin and exhibits superior stability.

10 Claims, No Drawings

ERYTHROPOIETIN LIPOSOMAL DISPERSION

FIELD OF THE INVENTION

The present invention relates to a liposome based formulation of erythropoietin. In particular, the invention relates to a liposome based parenteral dosage form of erythropoietin prepared by means of an ethanol injection technique which exhibits superior stability.

BACKGROUND OF THE INVENTION

Erythropoietin (EPO) is a glycoprotein which serves as the principal factor involved in the regulation of red blood cell synthesis. Erythropoietin is produced in the kidney and acts by stimulating precursor cells in the bone marrow causing them to divide and differentiate into mature red blood cells. The recombinantly produced 165 amino acid glycoprotein has been available for some time as an effective therapeutic agent in the treatment of various forms of anemia, including anemias associated with chronic renal failure, zidovidine treated HIV infected patients, and cancer patients on chemotherapy. The glycoprotein is administered parenterally, either as an intravenous (IV) or subcutaneous (SC) injection.

Presently, the parenteral formulations in use are conventional sterile buffered aqueous solutions for IV or SC injection which contain human serum albumin (HSA) as a carrier. Such formulations are marketed in the United States under the trade names EPOGEN® and PROCRIT®. These products contain erythropoietin in 1 ml single dose, preservative-free or 2 ml multidose preserved vials..

While these formulations have been proven to be highly successful, certain disadvantages are associated with the use of human serum albumin as carrier. As HSA is obtained from natural sources it can be a potential danger as a carrier for infectious disease agents such as HIV or hepatitis and careful screening of the material must be conducted. Further, the availability of appropriate quality of HSA can often be a problem. Hence, there is a need for an injectable formulation of erythropoietin which eliminates the use of HSA as a carrier.

Accordingly, attempts have been made to provide an improved formulation of erythropoietin which eliminates the use of HSA as a carier. At the same time the formulation should be stable and provide an extended shelf life. Further, the formulation must avoid problems associated with the active ingredient adhering to the surface of the vial in which it is contained.

Liposomes are small vesicles comprising amphipathic lipids arranged in spherical bilayers. Liposomes may contain many concentric lipid bilayers separated by aqueous channels (multilamellar vesicles or MLVs), or alternatively, they may contain a single membrane bilayer (unilamellar vesicles), which may be small unilamellar vesicles (SUVs) or large unilamellar vesicles (LUVs). The lipid bilayer is composed of two lipid monolayers having a hydrophobic "tail" region and a hydrophilic "head" region. In the membrane bilayer, the hydrophobic "tails" of the lipid monolayers orient towards the center of the bilayer, whereas the hydrophilic "heads" orient toward the aqueous phase.

Liposomes may be used to encapsulate a variety of materials by trapping hydrophilic compounds in the aqueous interior or between bilayers, or by trapping hydrophobic compounds within the bilayer. As such, they are particularly useful to deliver biologically active materials by encapsulating compounds which exhibit poor aqueous solubility or which exhibit unacceptable toxicity at therapeutic dosages.

A specific method for the production of liposomes with only one double layer is disclosed in EP 253 619. Liposome formulations of various active agents have been known for years and liposomal preparations of erythropoietin have been proposed. For example, Maitani et al, J. Pharm. Sci., 85:440–445 (1996) discloses liposomal erythropoietin formulations intended for oral administration in which the liposomes are prepared by the reverse phase evaporation vehicle method. Since the formulation therein is intended for oral administration, a high percentage of incorporation of EPO into the liposomes is preferred. However, formulations such as this demonstrating a high rate of encapsulation in small vesicles may exhibit concentration in the liver, leading to toxicities. Moreover, the manufacturing procedures used therein require special raw materials (e.g. polyglycerine phospholipid) and the use of organic solvents. Further, the reverse phase process used therein suffers a high loss of unencapsulated EPO, which is undesirable and expensive.

The goal of the present invention therefore was to provide a parenteral formulation suitable for EPO, which avoids the use of HSA as carrier, provides acceptable long term stability for an extended shelf life, and which can be manufactured by means of a process which is amenable to large scale manufacture.

SUMMARY OF THE INVENTION

A liposome-based parenteral composition comprising:
(a) an effective amount of an active ingredient comprising erythropoietin or its pharmaceutically acceptable derivatives having the biological properties of causing bone marrow cells to increase production of reticulocytes and red blood cells;
(b) a lipidic phase comprising:
   (i) lecithin or hydrogenated lecithin;
   (ii) optionally, a charged electropositive or electronegative lipid compound; and
   (iii) cholesterol or a derivative thereof selected from cholesterol esters, polyethylene glycol derivatives of cholesterol (PEG-cholesterols), and organic acid derivatives of cholesterols; and
(c) an aqueous buffer solution.

In accordance with the invention, the composition comprises single bilayered liposomes made by preparing an alcoholic solution of the lipidic phase and injecting the solution under pressure into an aqueous buffer solution contained in a high speed homogenizer. The liposomes thus prepared are incubated with the erythropoietin active ingredient to form the liposomal dispersion of the invention.

Preferably, the active ingredient is erythropoietin and its derivatives having the biological properties of causing bone marrow cells to increase production of reticulocytes and red blood cells. The EPO glycoprotein may be obtained from natural sources or produced recombinantly using known procedures as disclosed in U.S. Pat. Nos. 4,703,008, 5,441,868, 5,547,933, 5,618,698 and 5,621,080, hereby incorporated by reference.

In accordance with the present invention, it has been discovered that, quite unexpectedly, the liposomal EPO compositions prepared under the mild conditions described herein exhibit improved stability, i.e. the liposomes themselves are stable and at the same time the chemical degradation and aggregation of the biologically effective substance is minimized. As a further unexpected advantage, the EPO active ingredient does not adhere to the surface of the vial container or IV tubing even though the EPO is not substantially incorporated within the liposomes, but is instead essentially contained in the interstitial fluid as a liposomal dispersion.

DETAILED DESCRIPTION

The active ingredient used in the present invention is erythropoietin and its derivatives having the biological properties of causing bone marrow cells to increase production of reticulocytes and red blood cells. The liposomal dispersion of the present invention is useful as a parenteral formulation in treating blood disorders characterized by low or defective red blood cell production such as various forms of anemia, including anemias associated with chronic renal failure, zidovidine treated HIV infected patients, and cancer patients on chemotherapy. It may also have application in the treatment of a variety of disease states, disorders and states of hematologic irregularity such as sickle cell disease, beta-thalassemia, cystic fibrosis, pregnancy and menstrual disorders, early anemia of prematurity, spinal cord injury, space flight, acute blood loss, aging and the like. Preferably, the EPO composition of the present invention is administered parenterally (e.g. IV, IM, SC or IP). Effective dosages are expected to vary considerably depending on the condition being treated and the route of administration but are expected to be in the range of 0.1 (~7U) to 100 (~7000U) $\mu$g/kg body weight of the active material. Preferable doses for treatment of anemic conditions is about 50 to about 300 Units/kg three times a week.

The EPO liposomal dispersions of the present invention generally contain from about 200,000 Units to about 1 million Units of the EPO glycoprotein per 100 grams of composition. The active EPO ingredient is dispersed in a liposomal suspension formed from
 (a) a lipidic phase comprising:
  (i) lecithin or hydrogenated lecithin;
  (ii) optionally, a charged electropositive or electronegative lipid compound; and
  (iii) cholesterol or a derivative thereof selected from cholesterol esters, polyethylene glycol derivatives of cholesterol (PEG-cholesterols), and organic acid derivatives of cholesterols; and
 (b) an aqueous buffer solution.

Such a formulation, particularly produced according to the process described in EP 0 253 619, which is herein incorporated by reference, exhibits characteristics which make it a suitable substitute for the HSA containing compositions of the prior art.

Lecithin can either be used as natural lecithin in purified form or, preferably, as the more stable hydrogenated lecithin, whereby the use of the latter allows a reduction of the concentration of the stabilizing agents. The lecithin component is generally present in an amount from about 0.5 to 5.0 grams per 100 grams of composition. Preferably, the hydrogenated lecithin should be of good quality without detectable levels of catalysts which can influence the stability of EPO and liposomes in a negative manner.

Cholesterol is employed as the liposome stabilizing agent in amounts ranging from 0.1 to 1.0 grams per 100 grams of composition. In addition to cholesterol, other cholesterol derivatives may be employed such as cholesterol esters, polyethylene glycol derivatives of cholesterol (PEG-cholesterols), as well as organic acid derivatives of cholesterols, for example cholesterol hemisuccinate.

The electropositive or electronegative lipid is a lipidic compound having a positively or negatively charged component. Electropositive lipids are oleyl amine or stearyl amine. Electronegative lipids are oleic acids, phosphatidic acids such as dipalmitoyl phosphatidic acid (DPPA), di-palmitoylglycerole (DPPG), distearoyl phosphatidic acid (DSPA), or dimyristyl phosphatidic acid (DMPA). The use of such charged lipids yields charged liposomes which guarantee an opalescent dispersion preventing the liposomes from sedimentation. As stated, the result is quite unexpected that the active erythropoietin glycoprotein does not adhere to the glass walls of the container or the silicon tubing used for its administration even though the active ingredient is not incorporated within the liposomes but merely exists as a dispersion with the charged liposomes.

An alcohol component comprised of a lower alkanol of one to six carbon atoms, such as methanol, ethanol, n-propanol, isopropanol, n-butanol and the like in amounts ranging from 0.5 to about 5.0 grams per 100 grams of composition is generally included in the composition prepared by use of the ethanol injection technique. Ethanol is preferred.

The aqueous buffer component is selected from the typical acid salts conventionally used as buffers in parenteral compositons. Examples include the citrates, acetates and phosphates. A phosphate buffer is preferred. Examples include sodium dihydrogen phosphate dihydrate, or di-sodium hydrogen phosphate dihydrate, and mixtures thereof Preferably a mixture of sodium dihydrogen phosphate dihydrate and di-sodium hydrogen phosphate dihydrate in amounts ranging from 0 to 2.0 g/100 g is used.

Optionally, a stabilizer such as glycine can be added to the composition to prevent the formation of aggregates. However, in most cases such stabilizers are not necessary since the liposomes act as a stabilizer as well as a carrier in the composition.

The liposome-based compositions of the present invention are prepared by applying the methods known in the art for manufacturing liposome compositions described in EP 253619, hereby incorporated by reference. In this method single bilayered liposomes are prepared by preparing an ethanolic solution of a phospholipid and the active ingredient and injecting the solution under pressure into an aqueous buffer solution contained in a high speed homogenizer. The liposomes are formed spontaneously providing liposomes having a diameter of less than 1 $\mu$m. In particular, in accordance with the method of the present invention, the liposomes are manufactured by forming an aqueous buffer solution in purified water. Separately, the lecithin, cholesterol and charged lipid component are dissolved in an alcoholic solution such as ethanol. The aqueous solution is connected to a high performance homogenizer to effect circulation and the alcoholic solution is directly injected into the homogenizer. Liposomes of less than 1 $\mu$m are formed spontaneously. The liposomes thus formed are then incubated with the EPO active ingredient to form a liposomal dispersion of the invention.

To get a transparent liposome dispersion having liposomes with a well defined diameter, it is preferable to extrude the liposomes through filters with pores of about 0.05–0.08 mm resulting in liposomes with a diameter of about 80–100 nm. This additional particle sizing step is utilized to guarantee a transparent solution in order to easily detect any aggregations and to extend circulation time in the blood.

As stated above, the erythropoietin compositions currently marketed have stabilizers such as Tweens, amino acids etc. or are stored dry frozen to maintain stability and have limited shelf-life. It has been found that the liposomal compositions of the present invention exhibit excellent stability, i.e. the liposomes themselves are stable and at the same time the decomposition and aggregation of the biologically effective substance is minimized. A shelf-life of up to 2 years has been achieved which is very important for industrial application. This improved stability may be attributable to the superior mild manufacturing technology of the present invention and the ingredients and composition of the formulation (both from a qualitative and quantitative point of view when compared with the formulations described in the literature).

The stability of the composition can be further enhanced by the addition of antioxidants such as tocopherol, butylated hydroxytoluene, butylated hydroxyanisole, ascorbyl palmitate, or edetates such as e.g. disodium edetate, with the edetates additionally binding possibly present heavy metals. The stability can furthermore be enhanced by the addition of preserving agents such as benzoic acid and parabens, e.g. methylparaben, and/or propylparabene.

Preferred compositions are those of the following general formula:

|  | g/100 g |
| --- | --- |
| EPO or analogous compounds | 200,000 U–4 Mill. Units |
| Lecithin hydrogenated (Soya) | 0.5–5.000 |
| Cholesterol | 0.1–1.000 |
| Charged lipid | 0.05–0.5 |
| Ethanol | 0.5–5.000 |
| Glycine | 0.0–1.00 |
| Buffer | 0 to 2.0 |
| Water | q.s ad 100.0 |

The particular advantages of the present invention are further illustrated by the following examples:

EXAMPLE 1

Liposome-Based Dispersion

A liposome-based dispersion of the following composition was produced according to the method described in EP 0 253 619:

| Composition: | g/100 g |
| --- | --- |
| Erythropoietin | 1 Million I.U. |
| Lecithin (Soya) hydrogenated | 0.500 |
| Cholesterol | 0.100 |
| Ethanol Pharma Undenatured | 0.500 |
| Sodium Dihydrogenphosphate Dihydrate | 0.1164 |
| di-Sodium Hydrogen Phosphate Dihydrate | 0.2225 |
| Sodium Chloride | 0.584 |
| Water purified | 97.9771 |

Procedure

The liposomes are manufactured by forming an aqueous electrolyte (buffer) solution of the sodium dihydrogenphosphate dihydrate, di-sodium hydrogen phosphate dihydrate and sodium chloride in water for injection at 80° C.. Separately, the lecithin and cholesterol are dissolved in an alcoholic solution such as ethanol at 55° C.–70° C.. The aqueous solution is connected to a high performance homogenizer to effect circulation (kettle 1) and the alcoholic solution (kettle 2) is directly injected into the homogenizer. The ethanol solution was purged with nitrogen during the whole procedure. Liposomes of less than 1 $\mu$m are formed spontaneously. To form liposomes with a well defined diameter the liposomal dispersion was extruded through nucleopore filters with defined pores (e.g. 0.8 and 0.5 $\mu$m). Erythropoietin was incubated with the liposomal dispersion and later one sterile filtration. Filling of the vials was done under aseptic conditions.

Technical Data

Homogenizer speed: up to 13,000 rpm

Flow rate of the ethanol solution: 20–100 ml/s

EXAMPLE 2

| Liposome-Based Dispersion | |
| --- | --- |
| Composition: | g/100 g |
| Erythropoietin | 1 Million I.U. |
| Lecithin (Soya) hydrogenated | 0.500 |
| Cholesterol | 0.100 |
| DPPA-Na | 0.040 |
| Ethanol Pharma Undenatured | 0.500 |
| Sodium Dihydrogenphosphate Dihydrate | 0.1164 |
| di-Sodium Hydrogen Phosphate Dihydrate | 0.2225 |
| Sodium Chloride | 0.584 |
| Water purified | 97.9371 |

Procedure

The liposomal dispersion of Example 2 is prepared in accordance with the procedure of Example 1 with the exception that the DPPA-Na is added to the ethanol solution along with the lecithin and cholesterol prior to performing the ethanol injection.

EXAMPLE 3

| Liposome-Based Dispersion | |
| --- | --- |
| Composition: | g/100 g |
| Erythropoietin | 1 Million I.U. |
| Lecithin (Soya) hydrogenated | 0.500 |
| Cholesterol | 0.100 |
| DPPG-Na | 0.050 |
| Ethanol Pharma Undenatured | 0.500 |
| Sodium Dihydrogenphosphate Dihydrate | 0.1164 |
| di-Sodium Hydrogen Phosphate Dihydrate | 0.2225 |
| Sodium Chloride | 0.584 |
| Water purified | 97.9271 |

Procedure

The liposomal dispersion of Example 3 is prepared in accordance with the procedure of Example 2.

EXAMPLE 4

Stability Testing

Two batches of liposomal erythropoietin formulation were manufactured in accordance with the Examples 1 and 2. The batches were assayed for stability at various time intervals. The procedures for the in vitro and in vivo bioassays employed are set forth below. The results are set forth in Tables 1 and 2.

TABLE 1

Product: Erythropoietin Liposomal Formulation - Example 1
BN: uncharged liposomes
Dosage: 10,000 IU/ml

| Storage Time | Storage Conditions | Appearance | pH | EPO identity | ELISA | Bioassay |
|---|---|---|---|---|---|---|
| Initial | NA | pass | 6.86 | pass | 9695 | NA |
| 3 | 2–8° C. | pass | 6.97 | pass | 9194 | NA |
| 3 | 25° C. | pass | 6.98 | pass | 8715 | NA |
| 6 | 2–8° C. | pass | 7.07 | pass | 9925 | NA |
| 6 | 25° C. | pass | 7.08 | pass | 7886 | NA |
| 9 | 2–8° C. | pass | 7.01 | pass | 9452 | NA |
| 12 | 2–8° C. | pass | 7.02 | pass | 9452 | NA |
| 18 | 2–8° C. | N.A. | N.A. | pass* | 8635 | NA |
| 24 | 2–8° C. | pass | 7.05 | pass | 9200 | 8900** |

\* = <2% Aggregate standard ( 2% -AGG-1") by densitometry
\*\*in vivo mouse bioassay

TABLE 2

Product: Erythropoietin Liposomal Formulation
RN: negatively charged liposomes(Na-DPPA)
Dosage: 10,000 IU/ml

| Storage Time | Storage Conditions | Appearance | pH | EPO identity | ELISA | Bioassay |
|---|---|---|---|---|---|---|
| Initial | NA | pass | 6.71 | pass | 8757 | 10120 |
| 3 | 2–8° C. | pass | 7.03 | pass | 8776 | 8020 |
| 3 | 25° C. | pass | 7.02 | pass | 7854 | N.A. |
| 6 | 2–8° C. | pass | 7.02 | pass | 9621 | 7710 |
| 6 | 25° C. | pass | 7.06 | pass | 8453 | N.A. |
| 9 | 2–8° C. | pass | 7.03 | pass | 9189 | 8870 |
| 12 | 2–8° C. | pass | N.A. | pass* | 9150 | N.A. |
| 18 | 2–8° C. | pass | 699 | pass | 9003 | 9500** |
| 24 | 2–8° C. |  |  |  |  | NA |

\* = <2% Aggregate standard (2% -AGG-1") by densitometry
\*\*in vivo mouse bioassay, other are in vitro bioassay
In-vivo bioassay Exhypoxic polycythemic mouse erythropoietin bioassay. Mice remain at reduced pressure for 18 hours. The following 6 hours the mice remain at ambient pressure. This procedure is repeated the following 14 days. After 3 days at containing pressure erythropoietin is administered to the mice. After a day a solution containing $^{59}FeCl_3$ is injected. After another two days blood is analyzed and incorporation of $^{59}FeCl_3$ into erythrocytes is determined.

In-vitro Bioassay

The in-vitro bioassay is a cell-based bioassay designed to accurately quantitate the biological acitivity of epoetin alfa.

The samples are first diluted in tissue culture medium and then treated with cell cultures of HEP.G2. This adherent cell line retains the capacity of hepatic tissue in its ability to remove desialated proteins. A similar metabolic; process is known to occur in vivo, resulting in the reduced activity of desialated erythropoietin. Treatment with HEP.G2 cells will not remove sialated erythropoietin in epoetin alfa from the media. Thus, the in vitro bioassay mimics the mouse in vivo assay.

In the second step the remaining erythropoietin is separated from HEP.G2 cells and tested in a cell proliferation assay using the B6SUtA cell line. These cells grow in the presence of erythropoietin and the extent of growth is proportional to the amount of erythropoietin. Cell growth is subsequently measured by the amount of color produced when MTT is added to the cells. The color generated is directly proportional to the number of cells and reducing activity of the B6SUtA cells.

Conclusion

The data demonstrates a good stability of up to twenty-four months for both formulations.

We claim:

1. A liposomal-based parenteral composition comprising:
   (a) an aqueous phase comprising an aqueous buffer solution and erythropoietin or its pharmaceutically acceptable derivatives;
   (b) a lipidic phase comprising single bilayered liposomes made by preparing a solution of the following in an alcoholic solvent consisting of a lower alkanol of one to six carbon atoms:
      (i) lecithin or hydrogenated lecithin;
      (ii) a charged electropositive or electronegative lipid compound;
      (iii) and cholesterol or a derivative thereof selected from cholesterol esters, polyethylene glycol derivatives of cholesterol (PEG-cholesterols), and organic acid derivatives of cholesterol;
   and injecting the solution under pressure into the aqueous buffer solution contained in a high speed homogenizer;
   (c) said erythropoietin or its pharmaceutically acceptable derivatives being present in an effective amount and having the biological properties of causing bone marrow cells to increase production of reticulocytes and red blood cells, said erythropoietin being incubated with the single bilayered liposomes of step (b), thereby being dispersed within the external aqueous phase and being substantially unincorporated within the liposomes.

2. The liposome-based composition of claim 1, characterized in that it further comprises a stabilizer.

3. The liposome-based composition of claim 1, wherein the stabilizer is glycine.

4. The liposome-based composition of claim 1, wherein the charged electropositive or electronegative lipid compound is selected from dipalmitoyl phosphatidic acid (DPPA), di-palmitoylglycerole (DPPG), oleyl amine and stearyl amine.

5. The liposome-based composition of claim 1, Wherein the buffer is selected from sodium dihydrogen phosphate dihydrate, di-sodium hydrogen phosphate dihydrate, and mixtures thereof.

6. The liposome-based composition of claim 1, characterized in that it father comprises a preserving agent.

7. The liposome-based composition of claim 1, characterized in that it tinter comprises an antioxidant.

8. The liposome-based composition of claim 1, characterized in that it has the following composition:

|  | g/100 g |
|---|---|
| Erythropoietin or its pharmaceutically acceptable derivatives having the biological properties of causing bone marrow cells to increase production of reticulocytes and red blood cells | 200,000 U-1 Mill. Units |
| Lecithin hydrogenated (Soya) | 0.5–5.000 |
| Cholesterol | 0.1–1.000 |

-continued

|  | g/100 g |
|---|---|
| Charged lipid | 0.05–0.5 |
| Ethanol | 0.5–5.000 |
| Glycine | 0.0–1.00 |
| Buffer | up to 2.0 |
| Water | q.s ad 100.0 |

9. A method for treating anemia in a human in need of such treatment comprising administering a pharmaceutically effective amount of the liposome-based composition according to claim 1.

10. The liposome-based composition of claim 1, characterized in that it has the following composition:

|  | g/100 g |
|---|---|
| Erythropoietin | 1 Million I.U. |
| Lecithin (Soya) hydrogenated | 0.500 |
| Cholesterol | 0.100 |
| DPPA-Na | 0.040 |
| Ethanol Pharma Undenatured | 0.500 |
| Sodium Dihydrogenphosphate Dihydrate | 0.1164 |
| di-Sodium Hydrogen Phosphate Dihydrate | 0.2225 |
| Sodium Chloride | 0.584 |
| Water purified | 97.9371 |

* * * * *